United States Patent [19]

Webb

[11] Patent Number: 4,900,299
[45] Date of Patent: Feb. 13, 1990

[54] BIODEGRADABLE TAMPON APPLICATION COMPRISING POLY(3-HYDROXYBUTYRIC ACID)

[75] Inventor: Andrew Webb, Yarm, England

[73] Assignee: McNeil-PPC, Inc., Milltown, N.J.

[21] Appl. No.: 48,338

[22] Filed: May 11, 1987

[51] Int. Cl.[4] .............................................. A61F 13/20
[52] U.S. Cl. ........................................ 604/11; 604/14
[58] Field of Search ............... 604/367, 368, 370, 904, 604/1, 11, 13, 14, 15, 17, 16, 18, 904

[56] References Cited

U.S. PATENT DOCUMENTS

| | | | |
|---|---|---|---|
| 3,724,462 | 4/1973 | Hanke | 604/12 |
| 3,830,236 | 8/1974 | Hanke | 604/14 |
| 3,921,333 | 11/1975 | Clendinning et al. | 525/168 |
| 3,954,104 | 5/1976 | Kraskin et al. | 604/15 |
| 4,286,341 | 9/1981 | Greer et al. | 623/1 |
| 4,393,167 | 7/1983 | Holmes et al. | 525/64 |
| 4,412,833 | 11/1983 | Wiegner et al. | 604/14 |
| 4,477,654 | 10/1984 | Holmes et al. | 528/361 |
| 4,477,655 | 10/1984 | Holmes | 524/17 |
| 4,503,098 | 3/1985 | Potts | 604/381 |

Primary Examiner—C. Fred Rosenbaum
Assistant Examiner—Sharon Rose

[57] ABSTRACT

A biodegradable tampon applicator comprising a molded, flexible, polymeric hollow cylindrical body for enclosing a tampon therein and having a first open end through which said tampon is expelled and a second open end for receiving means for expelling said tampon, said body comprising a moldable poly 3-hydroxybutyric acid composition.

22 Claims, 1 Drawing Sheet

BIODEGRADABLE TAMPON APPLICATION COMPRISING POLY(3-HYDROXYBUTYRIC ACID)

BACKGROUND OF THE INVENTION

The present invention relates to tampon applicators and in particular to biodegradable tampon applicators formed of poly 3-hydroxybutyric acid (PHB).

Tampon applicators are not supposed to be disposed of via the sanitary and sewage systems. However, it is often the case that they are. A popular material for tampon applicators is polyethylene which is a non-degradable plastic. Thus disposal of polyethylene tampon applicators will cause accumulation and clogging in sanitary and sewage systems, in particular in septic tank systems. Furthermore such polyethylene applicators are not degraded in sewage treatment plants and are often passed out into the environment to be washed up on the shores of rivers, lakes and oceans. Thus it is a problem of the art to provide tampon applicators which overcome or ameliorate the sanitary and environmental disadvantages of those applicators commonly used.

U.S. Pat. No. 2518486 suggests the use of tampon applicators made of water-soluble polyvinyl alcohol. However, such applicators have been found to become sticky on contact with damp surfaces and to become relatively unstable in humid conditions. U.S. Pat. No. 3882869 is also directed to the problem of disposal of tampon applicators and proposes the use of a water soluble polymer compounded with filler material such as clay, talc, wood, flour or fibres. Such applicators are said to have a lower tendency to adhere to moist human tissue. Nevertheless, they are still formed of water-soluble polyvinyl alcohol with the inherent disadvantages thereof. U.S. Pat. No. 3954104 discloses a thermoplastic, water-dispersible, biodegradable composition which can for example be used to make a tampon applicator. The composition comprises hydroxycellulose which is biodegradable and water-soluble and starch as a biodegradable filler. Again these tampon applicators contain a water soluble material.

U.S. Pat. No. 4372311 seeks to solve this problem by providing disposable articles made from a water-soluble polymer, a surface of which articles being coated with a degradable water-insoluble polymer. The disposable articles include diapers, tampons, tampon applicators, sanitary napkins, bed liners and bandages. It is acknowledged that the utility of articles made from a water-soluble polymer is limited because even casual contact with moisture will cause the surface to become tacky or slippery thus interfering with the proper function of the article. Thus U.S. Pat. No. 4372311 proposes coating the water-soluble polymer with a water-insoluble polymer for protection. Poly $\beta$-hydroxybutyrate is one of a number of degradable water-insoluble polymers which, it is stated, may be used as a coating. The coating may be applied for example by dipping, spraying or brushing.

Further attempts to solve the problem of providing disposable tampon applicators that are stable on storage have involved the study of paper or cardboard applicators. These are generally unsatisfactory because of poor durability in handling, packaging and use; they have a low crush resistance, poor bending strength and relatively poor frictional characteristics. Furthermore, they absorb relatively high quantities of moisture thereby enhancing the lack of durability.

SUMMARY OF THE INVENTION

A biodegradable tampon applicator is provided comprising a molded hollow cylindrical body of polymeric material for enclosing a tampon therein and having a first flexible open end through which said tampon is expelled and a second open end for receiving means, such as a plunger, for expelling the tampon.

In accordance with the teachings of this invention, the cylindrical body comprises a moldable poly 3-hydroxybutyric acid composition which preferably is a copolymer of 3-hydroxybutyric acid and 3-hydroxyvaleric acid residues. Preferably, the 3-hydroxyvaleric acid residues are present in the range of from about 5 to about 30 mol %, based on the total moles of 3-hydroxybutyric and 3-hydroxyvaleric acid residues present. The composition is further modified by including a plasticizer. The proportion of the 3-hydroxyvaleric acid residue in the polymer and the plasticizer quantity are so chosen as to provide a moldable composition resulting in a flexible product. In particular the melt flow time, as hereinafter defined, is limited to not more than 20 minutes and the final product is of such material that exhibits a modulus of elasticity of 0.2 to about 1.0 GPa.

DETAILED DESCRIPTION OF THE INVENTION

Figure 1:
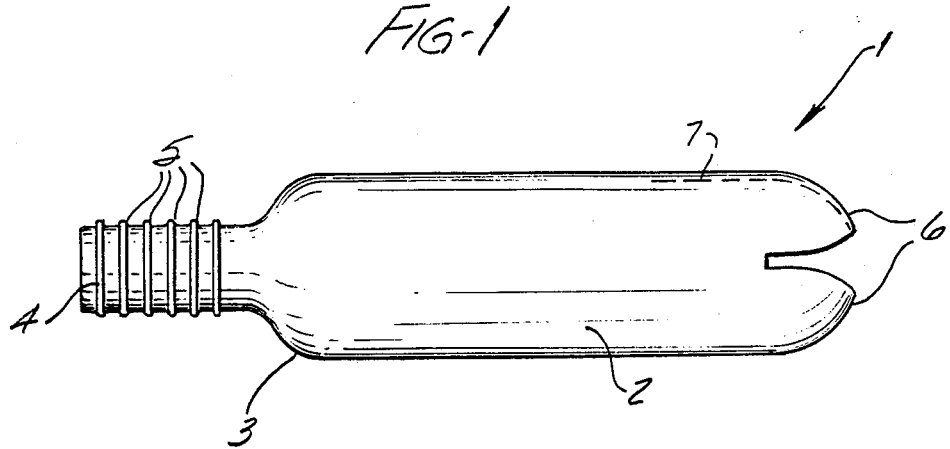
FIG. 1 illustrates a tampon applicator in longitudinal side view.
Figure 2:
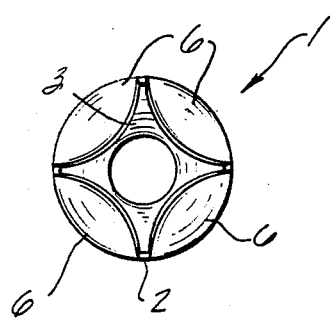
FIG. 2 illustrated the tampon applicator of FIG. 1 in end view.

The present invention provides tampon applicators that are biodegradable so that there is no blockage of sanitary and sewage systems. Furthermore there is significant benefit to the environment because of the biodegradability of the applicators. In addition the tampon applicators of the present invention are stable on storage, even in humid conditions, and exhibit the qualities and properties necessary for an applicator. In particular the applicators of the present invention are manufactured in one molding operation and are inexpensive and easy to make. The inherent disadvantages of a laminated or coated article are avoided.

Accordingly the present invention provides a tampon applicator comprising poly 3-hydroxybutyric acid.

Poly 3-hydroxybutyric acid is a thermoplastic polyester containing repeat units of the formula:

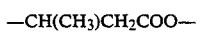

which is accumulated by many micro-organisms, in particular Alcaligenes, Athiorhodium, Azotobacter, Bacillus, Nocardia, Pseudomonas, Rhizobium and Spirillum as an energy reserve material.

Poly 3-hydroxybutyric acid is conveniently prepared by cultivating the micro-organism in an aqueous medium on a suitable substrate, such as a carbohydrate or methanol, as an energy and carbon source. The substrate must, of course, be one that is assimilable by the micro-organism. In order to promote the assimilation of the polymer, at least part of the cultivation is preferably conducted under conditions wherein there is a limitation of a nutrient that is essential for growth of the micro-organism but which is not required for polymer accumulation. Examples of suitable processes are described in EP-A-15669, 46344 and U.S. Pat. Nos. 4336334 and 4433053.

The polymer can be extracted from the bacterial cells by a variety of techniques, often involving a solvent extraction step. Examples of such processes are described in EP-A-15123.

Polymers containing both 3-hydroxybutyric acid units and other hydroxycarboxylic acid units, such as 3-hydroxyvaleric acid units can also be produced microbiologically. A microbiologically produced heteropolymer containing 3-hydroxybutyric acid and 3-hydroxyvaleric acid residues is described by Wallen et al. in "Environmental Science and Technology" 8 (1974) 576–9. In addition EP-A-52459 and 69497 and U.S. Pat. No. 4477654 describe that various copolymers, comprising poly 3-hydroxybutyric acid, can be produced. Cultivating on certain substrates varies the copolymer, for example propionic acid given rise to 3-hydroxyvaleric acid units in the copolymer.

Accordingly, in the present specification, the term "poly 3-hydroxybutyric acid", when mentioned in the context of the present invention, covers the homopolymer and copolymers wherein 3-hydroxybutyric acid units form at least 40 mol % and preferably at least 50 mol % of the polymer chain.

Poly 3-hydroxybutyric acid is non-toxic, compatible with living tissue without rejection or irritation and indeed the degradation product, 3-hydroxybutyric acid, is a normal mammalian metabolite.

There has been a number of disclosures on the processing of poly 3-hydroxybutyric acid in order to form shaped articles, for example U.S. Pat. Nos. 4360488, 4427614, 4477655 and 4537738. Poly 3-hydroxybutyric acid, in the present invention, can be processed in any convenient manner to form the tampon applicators.

Poly 3-hydroxybutyric acid homopolymer has a melting point of about 180° C. and the glass transition temperature (Tg) of the polymer is about 0° to 5° C. Poly 3-hydroxybutyric acid copolymers (with poly 3-hydroxyvaleric acid) have lower melting-points and have a similar glass transition temperature. The melting-point will depend on the proportion of 3-hydroxyvalerate units, for example, material having about 25% of such units will have a melting-point of about 105° C.

In order that a poly 3-hydroxybutyric acid polymer can be successfully injection molded or extruded, we have found it preferable that the melt-flow time is not more than 20 minutes when assessed by the following procedure:

The polymer composition (3.5 g) is charged to the barrel of a melt-flow grader (Daventest, Welwyn, England) provided with a die having a circular orifice of 2 mm diameter and 8 mm land length. The barrel is maintained at a temperature of from 10° C. to about 20° C. above the melting-point of the highest melting polymer (e.g. 180°–190° C. for homopolymer). Polymer (3.5 g) is added and left for a 4½ minute warm-up period; a 2.16 Kg load is applied to the piston which has a weight of 0.16 Kg. The composition is extruded through the die and cut-offs taken at minute intervals. The cut-offs are weighed and weight vs time is plotted (the test is performed in accordance with ASTM D 1238-73). Typical melt flow index (MFI) values are given in Table 1.

Various homopolymer and copolymer compositions can be used in the present invention with consideration given to both ease of handling and processability during manufacture and to the eventual end use of the applicator. The composition of the copolymer can be varied according to the teachings of the art. Thus various copolymers are available for use and different copolymers give rise to different physical properties of the applicators and to various ease of processing. In a preferred aspect of this invention the poly 3-hydroxybutyric acid is a copolymer consisting of 3-hydroxybutyric acid and 3-hydroxyvaleric acid residues, the amount of 3-hydroxyvaleric acid residues being in the range 5–30 mol %. Such copolymers provide applicators with improved flexibility and improved toughness. Flexibility is an important characteristic in the use of the applicators and improved toughness enables the walls of the applicators to be thinner thus permitting said applicators to be lighter, improving the rate of biodegradation, enhancing cosmetic appearance and encouraging consumer acceptability. Preferably the proportion of 3-hydroxyvaleric acid residues in 10–20 mol %, for example about 15 mol %.

For ease of processing a polymer composition that molds well is preferred. In general the lower the proportion of 3-hydroxyvaleric acid residues the greater the ease of molding, that is the greater the degree of crystallinity leading to shorter cycle times and lower melt degradation. However, we have found that the lower the proportion of 3-hydroxyvaleric acid residues then the stiffer the polymer composition is. Accordingly it is usually necessary to include at least one plasticizer to provide a polymer composition having suitable properties, for example reduced modulus of elasticity or increased toughness. In general the lower the proportion of 3-hydroxyvaleric acid residues the greater the amount of plasticizer that is required. A preferred range for the modulus of elasticity of the polymer compositions for use in this invention is 0.2–1.0 GPa, in particular 0.3–0.6 GPa and typically about 0.4 GPa. (giga Pascals)

Suitably the total amount of plasticizer used can be up to 40 parts per hundred of polymer resin (phr), for example, 40 phr of plasticizer can be used with a copolymer containing 5 mol % of 3-hydroxyvaleric acid residues. More conveniently, however, for a copolymer having 10–20 mol % of 3-hydroxyvaleric acid residues the preferred amount of plasticizer is in the range 10–30 phr for example about 20 phr. The amount of plasticizer used will also, of course, vary according to the specific plasticizer compound used. Suitable plasticizers include diacetin (Unichema), dibenzoate (Lankroflex SP80; Lankro), triethyl phosphate, alkylarylphosphate (Santiciser 141; Monsanto) iso-decyl diphenyl phosphate (Santiciser 148), butylbenzyl phthalate (Santiciser 160), neopentyl glycol (Benzoflex 8312; Velsicol Chemical Corporation), p-toluene sulphonamide (Santiciser 8) and dialkylalkyleneoxide glutarate (Plasthall 7050; C P Hall Ltd) and mixtures thereof. Preferred plasticizers are Santiciser 8 and Plasthall 7050 and mixtures thereof, in particular about a 50:50 mixture thereof.

In another aspect the polymer composition can contain up to 5 phr of a nucleating agent to encourage crystallization on molding. Suitable nucleating agents include talc, micronized mica, alumina, silica, boron nitride, calcium carbonate and calcium hydroxyapatite. Of these we have found boron nitride to be most satisfactory. Typically the amount of nucleating agent is in the range 0.3–3 phr, for example 0.5–2 phr and conveniently about 1 phr.

The polymer composition can contain various other additives used in the polymer processing art to aid handling and processing, for example, molding aids such as stearate salts and esters. In addition, additives to improve the cosmetic appearance of the applicator can be included in the composition for example pigments and titanium dioxide. Such additives can be present in an amount sufficient to be effective, typically about 1 phr for pigments.

In another aspect the poly 3-hydroxybutyric acid polymer composition can further contain a biodegradable filler. The filler has not significantly affect the characteristics of the polymer but enables the amount of poly 3-hydroxybutyric acid to be lowered thus resulting in economic savings. Suitable fillers include starch and hydroxyalkyl cellulose which do not significantly affect molding properties even when present in proportions of up to about 40 phr. Preferably any such filter is starch which is relatively inexpensive. In addition, the use of starch is advantageous as we have found that the rate of biodegradability of polymer composition is increased with increasing proportions of starch.

EXAMPLE 1

A polymer composition was prepared having the following ingredients:

|  | phr |
|---|---|
| poly 3-hydroxybutyric acid/poly 3-hydroxyvaleric acid copolymer (mol. wt about 750,000) having 8% 3-hydroxyvaleric acid units |  |
| Santiciser 8 | 10 |
| Plasthall 7050 | 10 |
| Boron nitride (from Fluorochem Glossop, U.K.) | 1.0 |
| Titanium dioxide | 1.0 |

This was molded using a Negri Bossi NB 90 (38 mm diameter screw) machine, having a cycle time of about 40 seconds, to provide tampon applicators each weighing about 1.9 g. The machine was operated using barrel temperatures in the range of 120°–180° C., and mold temperatures in the range of 30°–70° C., for example 40° C.

FIG. 1 shows a tampon applicator 1 having a hollow cylindrical body 2 about 55 mm in length and about 15 mm in diameter. The body 2 has at one end thereof a shoulder 3 to which is integrally molded a hollow cylindrical grip portion 4 of about 0.75 mm wall thickness having annular ribs 5. At the other end of the body 2 are integrally molded four flexible petals 6. Each petal 6 is of approximate elliptical shape and has a maximum length of about 10 mm. The wall thickness is aproximately 0.7 mm in region 7 of the body 2 and is approximately 0.3 mm in the region of the petals 6.

In use a tampon (not shown) is inserted in the cylindrical body 2. A plunger (not shown), conveniently of a disposable material similar to that of the applicator, is pushed through hollow grip portion 4 to urge the tampon against the flexible petals 6 thereby opening them. Continued pushing of the plunger results in the successful expulsion of the tampon whereupon the applicator can be hygenically disposed of. Conveniently grip portion 4 is held by the thumb and middle finger while the index finger operates the plunger.

The biodegradability of the tampon applicators of the present invention was studied using the following procedure. Anaerobic digester units composed of sealed glass bottles fitted with gas exhaust tubes whereby the gas expelled by the unit can be measured were prepared containing about 700 to 800 ml of anaerobic digested sludge to which fresh raw sewage had been added. Various tampon applicators according to the present invention were added and the units were sealed. Identical control units were also prepared without applicators. The gas produced was collected and measured daily and samples were removed periodically to determine the extent of actual solids degradation. The results for a number of applicators are given below:

Results

All applicators were as described above in relation to the drawings; however, some were of thicker wall thickness wherein the approximate wall thicknesses of the grip, body and petals were 1.1 mm, 0.85 mm and 0.45 mm respectively.

| SAMPLE | DESCRIPTION | DRY WEIGHT (g) |
|---|---|---|
| 1A | Thin wall Composition of Example 1 | 1.93 |
| 1B | Thin wall Composition of Example 1 | 1.945 |
| 2A | Thick wall Composition of Example 1 | 2.31 |
| 2B | Thick wall Composition of Example 1 | 2.30 |
| 3A (two samples) | Thick wall Composition of Example 1 | 2.49 / 2.48 |
| 3B (two samples) | Thick wall Composition (19% HV units) having Santiciser 8  5 phr / Plasthall 7050  5 phr / TiO₂  1 phr / Boron Nitride  1 phr | 2.50 / 2.50 |

| PRODUCT RECOVERY (% Weight Remaining) | | | | | | | | | |
|---|---|---|---|---|---|---|---|---|---|
|  | Day | | | | | | | | |
| Sample | 0 | 5 | 10 | 15 | 20 | 25 | 30 | 35 | 40 |
| 1A | 100 | 87 | — | 39 | — | 6 | — | 0 | — |
| 1B | 100 | 91 | — | 36 | — | 1 | — | 0 | — |
| 2A | 100 | 92 | — | 57 | — | 31 | — | 16 | — |
| 2B | 100 | 91 | — | 63 | — | 40 | — | 20 | — |
| 3A | 100 | 92 | 87 | — | 44 | — | 18 | — | 0 |
| 3B | 100 | 96 | 90 | — | 54 | — | 27 | — | 5 |

In all cases the non-recovered residual material was totally soluble and not detected by gross examination of the sewage sludge.

TABLE 1
TYPICAL MELT FLOW INDEX (MFI) VALUES FOR VARIOUS SAMPLES

| Sample | MFI | T_D (doubling time) in minutes |
|---|---|---|
| HV Units 6% Santiciser 8  5 phr Plasthall 7050  5 phr BN  1 phr TiO₂  1 phr | 0.48 at 170° C. | 6.6 |
| HV units 16% Santiciser 8  7½ phr Plasthall 7050  7½ phr BN  1 phr TiO₂  1 phr | 1.0 at 160° C. | 12 |
| HV units 19% Santiciser 8  5 phr Plasthall 7050  5 phr BN  1 phr TiO₂  1 phr | 0.61 at 160° C. | 11.1 |

What is claimed is:

1. A biodegradable tampon applicator comprising a molded, hollow cylindrical body of polymeric material enclosing a tampon therein and having a first flexible open end through which said tampon is expelled and a second open end for receiving means for expelling said tampon, said body comprising a moldable poly 3-hydroxybutyric acid composition.

2. The tampon applicator of claim 1 wherein said poly 3-hydroxybutyric acid is a copolymer comprising 3-hydroxybutyric acid and 3-hydroxyvaleric acid residues.

3. The tampon applicator of claim 2 wherein said 3-hydroxyvaleric acid residues are present in the range of from about 5 to about 30 mol %, based on the total moles of 3-hydroxybutyric and 3-hydroxyvaleric acid residues present.

4. The tampon of claim 3 wherein said 3-hydroxyvaleric acid residues are present in the range of from about 10 to about 30 mol %, based on the total moles of 3-hydroxybutyric and 3-hydroxyvaleric acid residues present.

5. The tampon applicator of claim 1 wherein said body further comprises a plasticizer in an amount sufficient to impart the material of said body with a modulus of elasticity of from about 0.2 to about 1.0 GPa.

6. The tampon applicator of claim 5 wherein said plasticing is in an amount sufficient to impart the material of said body with a modulus of elasticity of from about 0.3 to about 0.6 GPa.

7. The tampon applicator of claim 5 wherein said plasticizer is present in an amount of less than 40 parts per hundred parts (by weight) of polymer.

8. The tampon applicator of claim 7 wherein said plasticizer is present in an amount of from 10 to about 30 parts per hundred parts by weight of polymer.

9. The tampon applicator of claim 5 wherein said plasticizer is selected from the group consisting of diacetin, dibenzoate, triethyl phosphate, alkylarylphosphate, iso-decyl diphenyl phosphate, butylbenzyl phthalate, neopentyl glycol, p-toluene sulphonamide, dialkylalkyleneoxide glutarate and mixtures thereof.

10. The tampon applicator of claim 9 wherein said plasticizer comprises a mixture of p-toluene sulphonamide and dialkylalkyleneoxide glutarate.

11. The tampon applicator of claim 1 including a nucleating agent.

12. The tampon applicator of claim 1 including a biodegradable filler.

13. A method for making a tampon applicator comprising employing a composition comprising a copolymer of 3-hydroxybutyric acid and 3-hydroxyvaleric acid residues and a plasticizer; the mol % of said 3-hydroxyvaleric acid residues and the quantity of plasticizer selected to result in said composition having a melt flow time of not more than 20 minutes and when molded to result in a material having a modulus of elasticity of 0.2 to 1.0 GPa molding said composition into a hollow cylindrical body, and inserting a tampon therein.

14. The method of claim 13 wherein said material has a modulus of elasticity ranging from about 0.3 to about 0.6 GPa.

15. The method of claim 13 wherein said 3-hydroxybutyric acid residues are present in the range of from about 5 to about 30 moles %, based on the total moles of 3-hydroxybutyric and 3-hydroxyvaleric acid residues present.

16. The method of claim 15 wherein said 3-hydroxybutyric acid residues are present in the range of from about 10 to about 30 mol %, based on the total moles of 3-hydroxybutyric and 3-hydroxyvaleric acid residues present.

17. The method of claim 13 wherein said plasticizer is present in an amount of less than 40 parts per hundred parts (by weight) of polymer.

18. The method of claim 17 wherein said plasticizer is present in an amount of from about 10 to about 30 parts per hundred parts by weight of polymer.

19. The method of claim 13 wherein said plasticizer is selected from the group consisting of diacetin, dibenzoate, triethyl phosphate, alkylarylphosphate, iso-decyl diphenyl phosphate, butylbenzl phthalate, neopentyl glycol, p-toluene sulphonamide, dialkylalkyleneoxide glutarate, and mixtures thereof.

20. The method of claim 19 wherein the plasticizer comprises a mixture of p-toluene sulphonamide and dialkylalkyleneoxide glutarate.

21. The method of claim 13 including a nucleating agent.

22. The method of claim 13 including a biodegradable filler.

* * * * *